United States Patent [19]

Merten et al.

[11] 4,196,146

[45] Apr. 1, 1980

[54] MAKING NITRODIARYLAMINES FROM FORMYL DERIVATIVES OF AROMATIC AMINES AND NITROHALOARENES BY ADMIXING WITH CERTAIN AQUEOUS SALT SOLUTIONS

[75] Inventors: Helmut L. Merten, Hudson; Gene R. Wilder, Medina, both of Ohio

[73] Assignee: Monsanto Company, St. Louis, Mo.

[21] Appl. No.: 885,966

[22] Filed: Mar. 13, 1978

[51] Int. Cl.$^2$ .............................................. C07C 85/04
[52] U.S. Cl. ...................................... 260/576; 260/571
[58] Field of Search ................................ 260/576, 571

[56] References Cited

U.S. PATENT DOCUMENTS

| | | | |
|---|---|---|---|
| 2,442,952 | 6/1948 | Kitchens | 260/562 R |
| 2,924,620 | 2/1960 | Miller | 260/576 |

FOREIGN PATENT DOCUMENTS

| | | |
|---|---|---|
| 498077 | 12/1953 | Canada ...................................... 260/576 |
| 1056619 | 5/1959 | Fed. Rep. of Germany ........... 260/576 |
| 1455207 | 11/1976 | United Kingdom ...................... 260/576 |

OTHER PUBLICATIONS

Rondestvedt, "J. Org. Chem.," 42(10), pp. 1786–1790, (1977).

*Primary Examiner*—John Doli
*Attorney, Agent, or Firm*—Gordon B. Seward

[57] ABSTRACT

Forming nitrodiarylamines by gradually admixing, at condensation temperature for forming a nitrodiarylamine, to a mixture of the formyl derivative of an aromatic amine and a nitrohalobenzene, either A. aqueous potassium carbonate, or
B. aqueous potassium hydroxide and a member of the group consisting of potassium carbonate, tri-potassium phosphate, sodium tetraborate and potassium tetraborate and mixtures thereof, and concurrently removing water.

3 Claims, No Drawings

MAKING NITRODIARYLAMINES FROM FORMYL DERIVATIVES OF AROMATIC AMINES AND NITROHALOARENES BY ADMIXING WITH CERTAIN AQUEOUS SALT SOLUTIONS

The invention relates to the preparation of nitrodiarylamines which are valuable intermediates for the preparation of dyestuffs and antidegradants. For example, 4-nitrodiphenylamine is an important intermediate for rubber antidegradants. The invention particularly relates to the preparation of 4-nitrodiphenylamine from p-nitrochlorobenzene.

The catalyzed condensation of an aryl amine and an aryl halide to diarylamine is generally referred to as the "Ullmann condensation". An embodiment for the synthesis of p-nitrodiphenylamine attributable to I. Goldberg is the reaction of aniline, p-nitrochlorobenzene, alkali metal carbonate as acid acceptor and a copper catalyst as described for example in British Pat. No. 24,091 of 1906.

Merz found that the small amount of water formed by the neutralization of the hydrochloric acid by the carbonate had an inhibiting effect on the formation of p-nitrodiphenylamine and that the very small yield of about 1% obtained by the Goldberg synthesis could be increased about 70 fold by giving particular care and attention to the removal of the formed water from the reaction zone, P. L. Merz, U.S. Pat. No. 2,927,943, Mar. 8, 1960. Similarly, Miller reported that in reacting formanilide, bromobenzene potassium carbonate and an Ullmann condensation catalyst, best results were obtained using materials normally considered by those skilled in the art as anhydrous and continuously removing from the reaction zone water formed in the reaction. Robert K. Miller U.S. Pat. No. 2,924,620, Feb. 9, 1960.

By utilization of an acylated derivative as an activated form of the arylamine in the condensation with nitrohalobenzene and a so-called acid acceptor, usually potassium carbonate, it is possible to effect the condensation without the usual copper catalyst, British Pat. No. 855,719, published Dec. 7, 1960. However, it was found that the physical form of the potassium carbonate particularly the particle size, significantly influences the results.

It has now been discovered that the particle size of potassium carbonate can be eliminated as a variable and nitrodiarylamine produced with surprising efficiency by gradually mixing under condensation conditions an aqueous solution of potassium carbonate, nitrohaloarene and a formyl derivative of a primary aromatic amine and concurrently removing water from the reaction zone during the mixing and condensation.

It is believed that the role of potassium carbonate is to produce the potassium salt of the aforesaid formyl derivative in situ which becomes the immediate but transient precursor of the nitrodiarylamine product and potassium halide by-product. Hydrogen halide may not be formed at all. However, the exact mechanism of the unexpected results with aqueous potassium carbonate is unknown. Moreover, potassium carbonate is unique among the potassium salts examined per se.

Significantly, it has been further discovered that the reaction with aqueous potassium carbonate is substantially improved by using it with potassium hydroxide. More generally, it has been found that gradually mixing at condensation temperature while concurrently removing water, potassium hydroxide, nitrohaloarene, the formyl derivative of a primary aromatic amine and certain salts, notably: potassium carbonate, potassium bicarbonate, sodium tetraborate, potassium tetraborate, tri-sodium phosphate or tri-potassium phosphate or mixture thereof results in efficient production of nitrodiarylamine. Although per se an aqueous solution of none of the other salts is equivalent to aqueous potassium carbonate, the combinations with potassium hydroxide are all more effective. Aqueous potassium hydroxide per se is outside the present invention.

Preferably, the aqueous reactant is gradually added to a reactor at condensation temperature and the other reactants; namely, formyl derivative and nitrohaloarene independently are either already present in the reactor at condensation temperature or added concurrently with the aqueous reactant. The addition may be continuous but should be at a rate slow enough to avoid substantial build-up of water. It is believed that the process succeeds because the procedure minimizes hydrolytic side reactions. Thus, it appears that optimum operating conditions are realized by removing water at a temperature above about 170° at substantially the rate it appears in the reactor. The water which appears in the reactor comprises that added with the aqueous reactant and that formed in the condensation. The reaction temperature will usually be within the range of 140°–210° C., preferably 180°–200° C. The formyl derivative of the amine is preferably used in excess of the p-nitrohaloarene and recovered for use in subsequent reactions.

A variety of nitrohaloarenes have been proposed for making nitrodiarylamines, any of which appear to be suitable for use in the process of the invention. Illustrative of nitrohaloarenes believed to be suitable in the process are: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene, 1-chloro-2-nitronaphthalene, 3,4-dichloronitrobenzene, 3-methyl-4-chloronitrobenzene, 2-methyl-4-chloronitrobenzene, 2-ethyl-4-chloronitrobenzene, 2,3-dimethyl-4-chloronitrobenzene, 2,4-dimethyl-4-chloronitrobenzene, 3,5-dimethyl-4-chloronitrobenzene and p-nitrofluorobenzene.

The process is believed to be a general one for condensation of the formyl derivative of an aromatic primary amine. Suitable examples are formanilide and formanilide substituted in the benzene nucleus by one or more substituents inert under the reaction conditions; for example one or more alkyl, alkoxy, fluoro, chloro or nitro substituents. Illustrative substituted formanilides which may be used in the process are: m-chloroformanilide, p-chloroformanilide, 2-methylformanilide, 3-methylformanilide, 4-methylformanilide, 3-ethylformanilide, 3,4-dimethylformanilide, 3-methoxyformanilide, 4-methoxyformanilide, 4-ethylformanilide, 4-isopropylformanilide, 4-butylformanilide, 3,4-dichloroformanilide and 4-nitroformanilide.

DESCRIPTION OF PREFERRED EMBODIMENTS

EXAMPLE 1

Into a suitable reactor fitted with a condenser, water trap, stirrer and thermometer are charged 157 parts by weight (1.0 mole) of p-nitrochlorobenzene, 151 parts by weight (1.3 mole) of formanilide and 118 parts by weight of xylene. The mixture is stirred and heated at 185°–196° C. while there is gradually added to it over a period of about two hours a solution of 89 parts by weight of potassium carbonate in 89 parts by weight of water. During the addition, water is continuously removed and collected in the water trap. Stirring and heating are continued for about four hours after the addition of the carbonate solution. The reaction mixture is diluted with xylene, washed with water and the washed xylene solution cooled to induce crystallization of the 4-nitrodiphenylamine which is separated by filtration and dried to obtain 133 parts by weight. The mother liquor is analyzed for p-nitrochlorobenzene and 4-nitrodiphenylamine content and found to contain 17.2 parts by weight of 4-nitrodiphenylamine. The total yield is 70.2% and conversion of p-nitrochlorobenzene 97%.

EXAMPLES 2-6

Results are improved by using a mixture of potassium carbonate and potassium hydroxide. The reactions are carried out as described above, the potassium hydroxide being added to the potassium carbonate solution and the mixture added to the other reactions while removing water, the temperature being within the range of 174°–196° C. Xylene is used as inert solvent and distilled out until the desired temperature is reached. The moles of formanilide, $K_2CO_3$ and KOH per mole of p-nitrochlorobenzene (PNCB) are summarized in Table I.

TABLE I

| Example | Formanilide Moles per mole of PNCB | $K_2CO_3$ Moles per mole of PNCB | KOH Moles per mole of PNCB | Yield % | Conversion of PNCB % |
|---|---|---|---|---|---|
| 2 | 1.30 | .50 | .28[1] | 78.2 | 91.7 |
| 3 | 1.30 | .39 | .52[1] | 78.3 | 86.3 |
| 4 | 1.30 | .19 | .91[2] | 75.4 | 85.7 |
| 5 | 1.45 | .42 | .56[3] | 80.1[4] | 87[4] |
| 6 | 2.00 | .42 | .56 | 87.9 | 96.6 |

[1] added as 85% KOH to carbonate in 89 parts by weight of water
[2] added as 45% KOH to carbonate in 27 parts by weight of water
[3] added as 45% KOH to carbonate in 58 parts by weight of water per mole of PNCB
[4] figure is average of two runs The results in Table I show that yields from reaction with aqueous potassium carbonate solution are improved by adding potassium hydroxide to the solution.

EXAMPLES 7-15

Improvements are also observed by having the potassium carbonate or other salt present in the reaction mixture to which aqueous potassium hydroxide is gradually added at reaction temperature. In Examples 7-15, 0.55 moles of 45% aqueous potassium hydroxide (1.42 moles per mole of PNCB) is gradually added to a mixture of 65.4 grams (0.54 mole) of formanilide (1.4 mole per mole of PNCB) and 60.6 grams (0.385 mole) of p-nitrochlorobenzene and reaction promoter as indicated in Table II. Sufficient xylene is added to obtain the desired reaction temperature and the mixture heated to about 195° and the aqueous potassium hydroxide added at the rate of about 3 milliliters per minute while removing water. A rate of addition rapid enough to allow water to build up gives poorer results. Aqueous potassium hydroxide added to a reaction mixture in the absence of a reaction promoter is run as a control outside the invention. The control results are the average of three replicated experiments. The reaction promoter is given in Table II in terms of moles per mole of PNCB.

TABLE II

| Example No. | Reaction Promoter | Moles per Mole of PNCB | Yield % | Conversion PNCB % |
|---|---|---|---|---|
| — | None | — | 79.9 | 91.0 |
| 7 | $KHCO_3$ | .086 | 82.6 | 97.0 |
| 8 | $K_2CO_3$ | .073 | 84.4 | 98.8 |
| 9 | $Na_2B_4O_7 \cdot 10H_2O$ | .043 | 83.5 | 95.0 |
| 10 | $K_2B_4O_7 \cdot 4H_2O$ | .043 | 83.0 | 98.0 |
| 11 | $Na_3PO_4 \cdot 12H_2O$ | .043 | 84.2 | 94.9 |
| 12 | $K_3PO_4$ | .043 | 87.1 | 98.0 |
| 13 | $K_3PO_4$ | .018 | 84.2 | 94.3 |
| 14 | $K_3PO_4$ | .086 | 86.3 | 97.8 |
| 15 | $K_3PO_4$ | .26 | 85.9 | 99.3 |

As shown in Table II, improved yields are obtained by adding potassium carbonate to the refluxing reaction medium instead of to the aqueous solution to be admixed therewith. Although potassium bicarbonate and tri-potassium phosphate give significantly poorer results than potassium carbonate when added as aqueous solutions to p-nitrochlorobenzene and formanilide at reaction temperatures, they are effective promoters in combination with aqueous potassium hydroxide. The optimum amount of tri-potassium phosphate under the conditions described appears to be 0.043 moles per mole of p-nitrochlorobenzene. Under the conditions described, the amount of potassium hydroxide is a significant variable. For example, repeating Example 15 with 1.16 moles of KOH per mole of p-nitrochlorobenzene reduces the yield about 10%.

EXAMPLE 16

Into the reactor described in Example 1 are charged 85 grams (0.7 mole) of formanilide and 50 grams of xylene. The charge is heated to 185°–190° C. and there is fed thereto over a period of about 4 hours in separate streams 78.5 grams (0.5 mole) of p-nitrochlorobenzene and a solution of 29 grams (0.21 mole) of potassium carbonate in 35 grams (0.28 mole) of 45% potassium hydroxide. Heating is continued after the addition for 40 minutes at 180°. The 4-nitrodiphenylamine and unreacted p-nitrochlorobenzene are determined as described in Example 1. The yield of 4-nitrodiphenylamine is 62.1% and the conversion of p-nitrochlorobenzene 72.4%.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The process which comprises forming nitrodiarylamines by gradually mixing at condensation temperature for forming nitrodiarylamine the formyl derivative of an aromatic amine, nitrohalobenzene and aqueous potassium carbonate and concurrently removing water, wherein the aqueous potassium carbonate is added at a rate slow enough to avoid substantial buildup of water.

2. The process which comprises forming nitrodiarylamine by gradually mixing at condensation temperature for forming nitrodiarylamine
   (A) formanilide for formanilide substituted in the benzene nucleus with one or more alkyl, alkoxy, fluoro, chloro or nitro substitutents,
   (B) nitrohalobenzene and
   (C) aqueous potassium carbonate while removing water, wherein the aqueous potassium carbonate is added at a rate slow enough to avoid substantial buildup of water.

3. The process of claim 2 wherein A is formanilide and B is p-nitrochlorobenzene.

* * * * *